(12) United States Patent
Rasmussen et al.

(10) Patent No.: US 7,575,003 B2
(45) Date of Patent: Aug. 18, 2009

(54) DEVICE FOR DISPENSION

(75) Inventors: Jørgen Rasmussen, Struer (DK); Søren Christrup, Struer (DK)

(73) Assignee: Bang & Olufsen Medicom A/S, Struer (DK)

( * ) Notice: Subject to any disclaimer, the term of this patent is extended or adjusted under 35 U.S.C. 154(b) by 289 days.

(21) Appl. No.: 10/533,782

(22) PCT Filed: Nov. 1, 2003

(86) PCT No.: PCT/DK03/00749

§ 371 (c)(1),
(2), (4) Date: May 26, 2005

(87) PCT Pub. No.: WO2004/041334

PCT Pub. Date: May 21, 2004

(65) Prior Publication Data

US 2005/0268905 A1    Dec. 8, 2005

(30) Foreign Application Priority Data

| Nov. 4, 2002 | (DK) | ................................ 2002 01694 |
| Nov. 4, 2002 | (DK) | ................................ 2002 01695 |
| Mar. 20, 2003 | (DK) | ................................ 2003 00429 |
| Jul. 11, 2003 | (DK) | ................................ 2003 01053 |

(51) Int. Cl.
*A61M 11/00* (2006.01)
*A61M 15/00* (2006.01)

(52) U.S. Cl. .......................... 128/200.23; 128/200.14; 128/203.12; 128/203.23; 128/204.18; 128/205.23; 222/635

(58) Field of Classification Search ............ 128/200.11, 128/200.12, 200.14, 200.17, 200.21, 200.23, 128/203.12, 203.15; 222/635; 220/915
See application file for complete search history.

(56) References Cited

U.S. PATENT DOCUMENTS

| 4,678,106 | A |   | 7/1987 | Newell et al. |
| 4,834,083 | A |   | 5/1989 | Byram |
| 5,119,806 | A |   | 6/1992 | Palson |
| 5,447,150 | A |   | 9/1995 | Bacon |
| 5,623,920 | A |   | 4/1997 | Bryant |
| 5,692,492 | A | * | 12/1997 | Bruna et al. ............ 128/200.23 |
| 6,360,739 | B1 | * | 3/2002 | Rand et al. ............. 128/200.23 |
| 6,405,727 | B1 |   | 6/2002 | MacMichael |
| 6,672,304 | B1 |   | 1/2004 | Casper |
| 2001/0013343 | A1 |   | 8/2001 | Andersson |
| 2002/0073996 | A1 | * | 6/2002 | O'Leary ................. 128/203.15 |
| 2002/0157664 | A1 |   | 10/2002 | Fugelsang |

FOREIGN PATENT DOCUMENTS

| EP | 0254391 | 4/1987 |
| EP | 0476991 | 9/1991 |
| EP | 1008361 | 12/1999 |
| GB | 2264238 | 5/1992 |
| WO | 9949916 | 3/1999 |

OTHER PUBLICATIONS

Webster's New World Dictionary, Third College Edition, 1988, p. 1550.*

* cited by examiner

*Primary Examiner*—Justine R Yu
*Assistant Examiner*—Clinton Ostrup
(74) *Attorney, Agent, or Firm*—James Creighton Wray; Maera P. Narasimhan

(57) ABSTRACT

The present invention relates to a device for dispensing a medicament from a pressurised canister comprising a mouthpiece, a seat for engagement with the top of the canister and a housing provided with means for guiding and/or holding the canister.

16 Claims, 6 Drawing Sheets

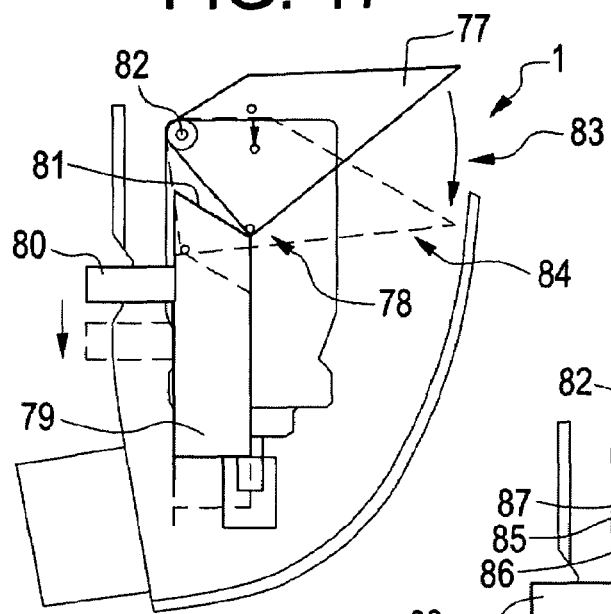
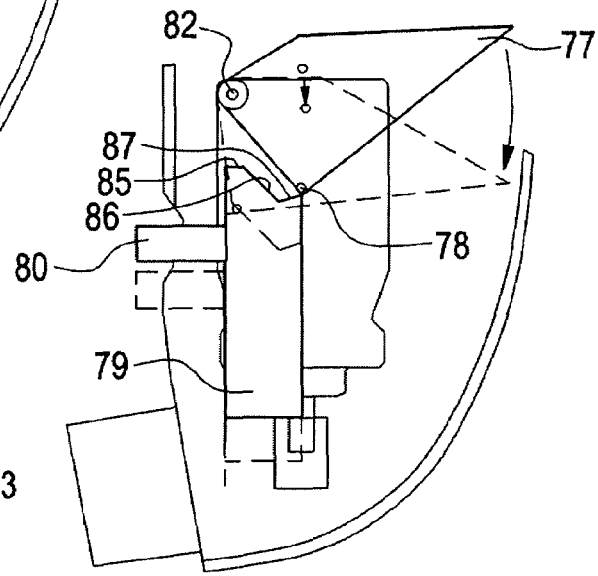
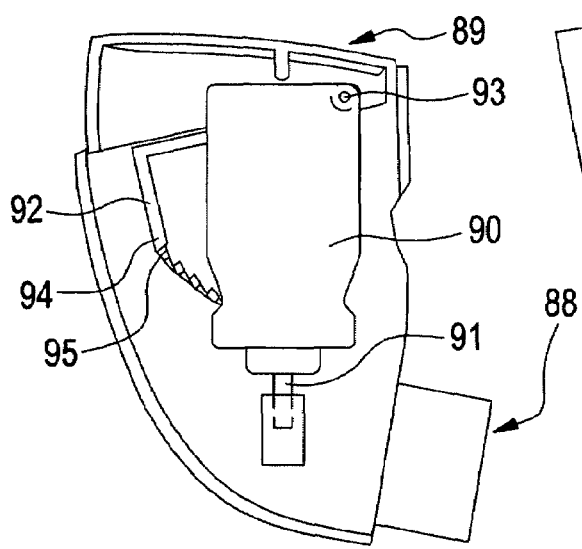
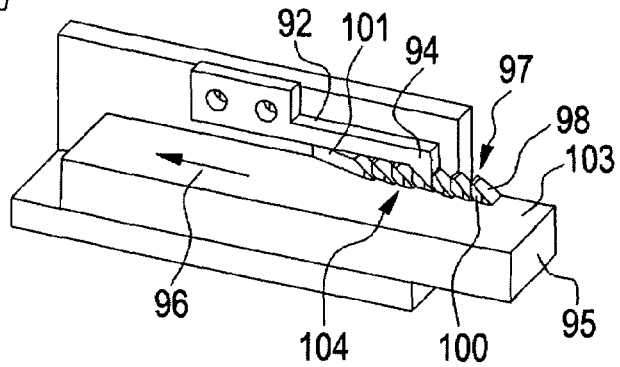

DEVICE FOR DISPENSION

This application claims the benefit of Danish Application No. 2002 01694 filed Nov. 4, 2002, Danish Application No. 2002 01695 filed Nov. 4, 2002, Danish Application No. 2003 00429 filed Mar. 20, 2003, Danish Application No. 2003 01053 filed Jul. 11, 2003 and PCT/DK2003/000749 filed Nov. 1, 2003, which are hereby incorporated by reference in their entirety.

FIELD OF THE INVENTION

The present invention relates to a device for dispensing a medicament from a pressurised canister where the device comprising a mouthpiece, a seat for engagement with the top of the canister and a housing provided with means for guiding and/or holding the canister.

BACKGROUND IF THE INVENTION

These types of devices are used as portable inhalation devices which permit the user to inhale a medicated vapour spray where the spray may include powders, liquids or gasses.

These types of devices are usually used by people suffering from asthma and other respiratory diseases or disabilities having difficulty breathing from time to time. Depending on the activity level of the person in question, the breathing difficulties may be more or less severe. Also inflammations or other infections or secondary diseases in the respiratory system can further aggravate the difficult breathing situation.

Asthma inhalation devices function in a way whereby the user/patient when needing to inhale the medication places the asthma inhalation device with a mouthpiece in the patient's mouth and thereafter activates a button. By depressing the button a canister inside the device is activated such that a medication dose stored in the valve system in the canister is dispensed through the mouthpiece to the patient.

A number of medications are available in order to alleviate these symptoms and substantially restore the individual's ability to breathe to a normal stable situation.

Although there are a number of different ways in which to take medications for alleviating the problems mentioned above, one of the more common types is to have the medication mixed with an aerosol propellant in a canister. The canister in then placed in an inhalation device whereafter the individual suffering from breathing problems can insert a mouthpiece into the mouth and by depressing the canister in the device dispense a dose of the medication directly into the airways.

The canister is usually placed upside down in the device, see for example EP 476991, such that the dispensing nozzle and/or the rim, i.e. the ferrule as well as the stem of the canister, are pointing downwards in the inhalation device. The stem rests on a seat and is guided such that upon depression of the canister by the user's hand into the device, the nozzle will be depressed and due to the overpressure created by the propellant in the canister, a dose will be sprayed into the user's mouth. The user will then inhale the aerosolised medication directly into the lungs.

The device disclosed in EP 476991 further discloses a pivotable member, which in a closed position covers the mouthpiece and in an active position is pivoted into a position where the member engages the bottom of the canister and acts as a lever arm for depressing the canister.

It is a requirement that canisters of this type are fitted with a valve system whereby depression of the canister and thereby dispensing of medication through the stern/nozzle is provided such that only one single dose per compression will be dispensed.

Conventional dispensers are usually two-piece structures consisting of a housing which contains the mouthpiece which is also adapted to receive the aerosol canister wherein the medication is contained. The medication is contained in the canister under pressure due to the presence of an aerosol. The canister is inserted into the housing so that the dispensing nozzle of the canister is pointed downward and oriented towards the mouthpiece provided on the housing as is the case in EP 476991. The opposite end of the canister usually projects upwardly and outside the housing. The user can place the housing between the thump and forefinger and use the thump and forefinger or the thump and fingers to force the canister downward and in this way release a dose of the medication into the mouthpiece and thereby inhale it into the airways and lungs.

For individuals suffering from mild forms of asthma or other breathing disabilities, depressing the canister into the device and thereby dispensing a dose does usually not cause a problem. However, a large number of the users of these types of devices are also suffering from other debilitations such as rheumatism or arthritis. Furthermore, small children needing asthma medications may also find it difficult to grip the prior art devices as mentioned above in that their hand are physically to small in order to be able to grip around the device and exert the necessary force in order to dispense a dose. A number of devices are therefore proposed which should aid especially users with reduced physical ability to depress the canister in order to dispense a dose. Such devices are presented in U.S. Pat. No. 6,397,837, EP 476991 and U.S. Pat. No. 4,834,083 wherein the traditional inhalation device can be equipped with a lever arm device mounted on the traditional inhalation device.

One problem associated with some of the devices mentioned above is that the lever arrangement either must be installed before every dispensing of a dose. This can cause serious problems for the user in that usually when a dose is needed, the user's ability to breathe is hampered and the stress level for the user is therefore increased. In order to assemble the device such that a dose can be dispensed, more parts have to be relocated and assembled on the device. Another problem is that for a host of users it is desirable to carry the device around with them such that a dose can be dispensed whenever needed i.e. in the office; on the bus etc. For this purpose the users often carry their dispensing device in a pocket or in a small handbag. With the lever arm arrangement according to the prior art mentioned above there is a tendency that the lever arm may become stuck since it projects outside the general geometry of the device itself as seen in for example U.S. Pat. No. 6,397,837 and EP 476991. This in turns means that either the device will be broken off and therefore not function or the lever arm arrangement will be disassembled causing extra trouble for the user when a dose needs to be dispensed.

For a number of users suffering from diseases where the medication is dispensed in the manner described above they will have different canisters containing different concentrations of the medication or even different types of medication for different diseases. The canisters and/or devices are often colour-coded in order to provide information about the medications contained in the canister. It is however a problem for the user always to have the correct canister mounted in the device as well as some of the devices are made in such a way that it is impossible to recognise the colour-coding on the canister as usually a large part of the canister is placed inside the dispensing device. It is therefore foreseeable that a situation can arise where a person suffering from any of the debilitations mentioned above will find him/herself in a situation with the wrong medication and further might inadvertently dispense a dose of a wrong medicament due to the inability of recognising the canister in the device.

Depressing the canister in order to dispense a dose can require an amount of force which for some users creates uncertainty whether a dose has been fully dispensed or not, due to the user's limited strength. As a number of the users as explained above can have limited force in their hands it becomes increasingly difficult for these persons to dispense doses when needed.

Recently the legislative bodies in the different countries have made moves to ban the CFC-gasses which are traditionally used as aerosols in canisters of this type. CFC-gasses are being replaced by a new family of gasses known as HFA-gasses. These gasses when used as aerosols/propellants require that the gaskets and the valve arrangement in the canister are made in a different manner. For the user the result is that a higher force is needed in order to compress the canister into the inhalation device whereby the nozzle is sufficiently compressed for it to dispense a dose of the medication. As a number of the users as explained above can have limited force in their hands it becomes increasingly difficult for these persons to dispense doses when needed. A further consideration both for producers and for the users of this type of device is the hygienic circumstance in which the device as a whole but especially the mouthpiece is manufactured, handled, stored and kept by the user.

Some patients suffering from asthma or other respiratory diseases often suffer from other related diseases such that it is important that the mouthpiece is kept as clean as possible.

In order to protect the mouthpiece, it is customary to provide a loose cap which snugly fits onto the mouth piece. This cap however, has a tendency to become lost, damaged or otherwise not fulfil its function. In order to alleviate this it has been suggested in the art to fasten the cap to the device itself, for example by means of a strap or to arrange a hinge such that the cap member can be pivoted into a closed position as is the case I EP 476991. In all the prior art devices where attachment means have been provided for keeping the cap in close proximity to the device as such, the cap can obstruct the usability of the device and hamper the dispensation of a medication dose.

A different solution is proposed in U.S. Pat. No. 4,834,083, where a cap is not provided as such. The space in which the nozzle and valve of the canister is placed is separated from the outside by a slidable closure gate.

The device as disclosed in U.S. Pat. No. 4,834,083 further discloses an arrangement for avoiding accidental dispensation of a dose. When the canister is placed inside the device, the lever arm is pivoted into a closed position covering the canister. The lever arm is provided with two projections—a latch and a stop. When closing the lever, the latch engages a hook section provided in the housing. The stop projects through an aperture in the housing for engagement with a catch. In order to prepare the device for use the gate shall be raised, whereby the gate shall deflect the stop from its engagement with the catch. As the lever is depressed, both the latch and the stop may be further deflected due to engagement with the housing in order for the lever to be able to move downwards. A number of drawbacks are connected with this construction. As the stop is arranged in a aperture in the housing and the gate acts on the stop adjacent the aperture, the forces needed for deflecting the member sufficiently are high. The deflection is, furthermore, limited by the latch which altogether hampers the depression of the canister. The space between the stop and the latch is very limited and if foreign matter becomes stuck, the operation of the device is severely obstructed.

On the other hand, after a number of deflections the stop may have attained a substantial permanent deflection such that accidental dispensation of a dose may occur. Production-wise is may also be difficult to control the process as the latch and stop members must be separated and precisely spaced and curved in order to be able to cooperated with corresponding elements in the housing.

In order to be able to describe the canister in detail and how the different parts and sections of the device are arranged in relation to each other, the relative terms "inside", "outside", "up", "down", "in front of" and "behind" shall be interpreted as imagining the device in the user's mouth in the use situation i.e. in a situation where a user is standing vertically and inserts the device having the canister in a substantially vertical position with the stem and nozzle section and ferrule of the canister placed such that the stem and nozzle can dispense a dose out through the mouthpiece. In this position the canister containing the medication is above the stem. Consequently, the bottom of the canister is the end with the ferrule and the stem/nozzle. The opposite end is designated the top. In front of the canister, means that it is close to the user's face i.e. on the same side as the mouthpiece, and behind the canister is to be understood as being away from the user's face. Inside the housing is to be interpreted as being within the volume comprised within the housing. Horizontal is consequently defined in relation to the above described use position.

SUMMARY OF THE INVENTION

Consequently, it is an object of the present invention to provide a device for dispensing a medicament as described above which provides for easy, reliable and safe dispensation of a dose and which furthermore alleviates the drawbacks of prior art devices as mentioned above.

One very important aspect of the invention is to provide for a reliable dose counting such that a user may rely on the information provided relating to the actual amount of doses left in the device.

General Device

The invention addresses this problem by providing an inhaler device for dispensing a medicament from a pressurised canister, where said device comprises a mouthpiece arranged in a housing, where said housing substantially encloses the canister, where a lever arm is provided, where said lever arm comprises means for engaging the bottom of the canister such that said lever arm may be activated by a user in order to dispense a dose, peculiar in that the lever arm further engages a yoke where the transfer of movement from said lever arm due to the activation of said lever arm to the yoke is linear and/or non-linear, and that the yoke comprises means for transferring the movement to a dose counting mechanism arranged in the housing.

By providing the transfer of the activation movement to the yoke, it becomes possible to control the input to the dose counting device. It is, as discussed above, known to use a lever arm in order to reduce the force necessary to dispense a dose. The actual movement of the canister in order to activate the valve of the canister is, however, very small. If the dose counter, therefore, is activated by the very limited movement of the canister, the occurrence of manufacturing tolerances, i.e. play in the device, may give rise to "false" counts. Therefore, by transferring the activating movement to a yoke, it becomes possible to both isolate and differentiate the activation movement into a dose dispensation and a counting movement.

In order to further exploit the possibilities of utilising the yoke, the movement of the canister caused by said lever arm in order to dispense a dose is shorter that the corresponding movement of said yoke.

In this manner, it is achieved that the very limited movement of the canister in order to dispense a dose is transformed into a relatively large movement in the yoke such that a more determined input may be delivered to the dose counting mechanism.

The invention further addresses the object stated above by providing a device for dispensing a medicament which is special in that a lever arm having means for engagement with the bottom end of the canister such that the canister is not accessible form the outside, where a seat for engagement with the top of the canister is provided inside the housing, and a cap is pivotally arranged such that the cap can be pivoted into a closed position where it covers the mouthpiece and an open position where the mouthpiece is accessible, and that said cap further comprises means for abutting the top of the canister and/or for abutting the means for engagement with the bottom end of the canister when the cap is in its closed position such that the canister cannot be activated accidentally By providing a lever arm, the amount of force needed by the user to depress the canister is lessened. This is especially important with the new type of propellants/aerosols in that the seals and gaskets in the canister around the nozzle makes it more difficult i.e. requires higher forces in order to compress the canister enough for a dose of medication to be dispensed.

Contrary to prior art devices, in a preferred embodiment the lever arm is only projecting outside the housing when the means for engagement of the bottom end of the canister is engaging the canister.

Alternatively, the lever arm is provided flush with the housing. The lever arm still provides the advantages as explained above, but additionally provides for a simpler construction. In use this embodiment provides the user with more possibilities for holding and activating the device. At the same time when the lever arm is a free moving part, but integral/flush with the outer surface of the device, easy and unhindered storage of the device is assured. Furthermore, foreign matter cannot enter the device and accidentally hinder activation of the drug dispensation or an optional dose dispensing device. In one actual embodiment of the device the lever arm is the activating button. The button is arranged such that an air gap between the button and the housing lets in the air required for being able to inhale the dispensed dose through the mouthpiece.

Furthermore, as there are no projecting members of the device, it becomes easier to store in a pocket, handbag or the like and furthermore the risk of damaging the device is minimal due to the protective housing surrounding the device as such.

Turning to the more specific construction of the device, the device in a further preferred embodiment of the invention is constructed such that the means for engaging the bottom of the canister are integral with the lever arm. When the lever arm and the means for engaging the bottom of the canister is one and the same member, for example constituting an outside surface of the housing, fewer parts are needed in the assembly of the device. This has some advantages in the fact that the fewer parts comprised in the device, the fewer parts can be misassembled or malfunction during the device's expected lifetime. Furthermore, by integrating the means for engaging the bottom of the canister in the lever arm, the effect of the lever arm is maintained and the device is presented as an integral unit without any members extending substantially outside the housing of the device, especially when the cap is in its closed position.

The lever arm's function is mainly to reduce the force necessary to dispense a dose as explained above. This is particularly true for the canisters comprising HFA-propellants/aerosols where gaskets of a different type are needed in order to make the canister leak proof. These gaskets require a higher force in order to depress the canister for dispensing a dose. The lever arm is therefore in a further preferred embodiment constructed such that the lever arm has a length corresponding to increasing the actual force delivered to the bottom of the canister by the engagement means by a ratio in the range of from 2:1 to 5:1, most preferred around 3:1.

A further advantage in increasing the force transferred to the canister is that it is assured that a positive dispensation and complete depression of the canister can be obtained since it will be easier for the user to depress the lever arm completely. Also by providing a lever arm, the need to use force by the user diminishes in that the lever arm multiplies the force. Furthermore, a better coordination between the activating movement e.g. the depression of the lever aim and the inhaling of the dispensed dose is achieved.

In a further preferred embodiment, the lever arm is a pivotal section of the housing constituting at least part of the top surface of the device and the lever arm is pivotally fastened to the housing in one end of the lever arm. Also in a still further embodiment, the lever arm adjacent its free end comprises a downwardly projecting hook section and a corresponding grip section is arranged on the inside of the housing such that the hook and the grip section can be brought into abutting contact and thereby create a snap-joint.

As the lever arm in this embodiment of the invention also is a part of the housing, it is important for the integrity of the housing that the lever arm is kept in a position where it is flush with the rest of the housing. The hook and grip sections when engaged by the snap-action creating the snap-joint provide for the downward depression movement of the lever when the means for engaging the bottom of the canister is activated such that an unproblematic ejection of a dose can be performed. When the canister moves back up and thereby pushes the engagement section up. The upward movement of the canister is limited by its ability to reset and the lever arm being a section of the housing has a limited movement due to the fact that the hook section abuts the grip section. By adjusting these two, it is possible to ensure that the lever arm does not engage the bottom of the canister and at the same time that the surface of the lever arm is kept at a level where the top surface of the lever arm is substantially flush with the rest of the housing.

The Cap

By further providing a cap for covering the mouthpiece it is achieved that the part of the device adapted to be inserted into the oral cavity of the user is kept as cleans as possible. The cap is pivotally mounted to the housing such that it can pivot between a closed position where the mouthpiece is completely covered and an open position in which the mouth piece is accessible.

The pivotally mounted cap makes sure that the cap is always available for covering up the mouthpiece when the mouth piece is not to be used. Although this does not constitute a 100% hygienic protection for the mouth piece, it does provide protection against dust, sand and other foreign objects which might otherwise become stuck either inside the mouthpiece or on the surface of said mouth piece. By being able to pivot the cap away from covering the mouth piece and into an open position where the mouthpiece is not hindering the access to the mouth piece, both the hygienic protection of the mouthpiece as well as the safe keeping of the cap is assured.

Additionally, the cap comprises means which means in the caps closed position abuts/engages the top of the canister, whereby downward movement of the canister is prevented and thereby prevents the dispensing of a dose. By positively locking the canister in this position wherein it is impossible for it to be activated in order to dispense a medicine dose through the nozzle, it is assured that the device as such will not dispense a dose inadvertently. It requires a positive action from the user side, namely the pivoting of the cap member in order to firstly gain access to the mouthpiece through which inhalation of the medication is done and at the same time releasing the canister from a locked position such that upon activation of the means for engaging the bottom of the canister, the top of the canister including the nozzle means can be brought into a position where a medication dose can be dispensed.

The means for abutting/engaging may alternatively act on the means for engagement with the bottom end of the canister when the cap is in its closed position such that the canister cannot be activated accidentally.

In a further advantageous embodiment a shaft projecting out of the housing engages at least one aperture provided in the cap or a depression on the inside of the cap. This arrangement can, however, also be arranged such that the depression or aperture is arranged in the housing and the engaging shaft is provided on the cap. On the inside of the cap adjacent the aperture or depression a cam is provided. The hinge-like arrangement of the cap constitutes a simple and a cost effective way of arranging the cap on the housing.

In a further advantageous embodiment the means for engagement with the bottom of the canister comprise a yoke which yoke has a canister engagement section optionally having a shape corresponding to the bottom of the canister and an end section which, when the cap is in its close position, engages the cam provided on the cap such that the engagement section of the yoke is not in contact with the canister.

This mechanism makes certain that the engagement means not accidentally can be activated and the canister depressed. By depressing the canister, the nozzle will be activated and a dose will be dispensed. It is therefore not desirable to have an uncontrolled dispensing of medication. This is assured by having a mechanism which, when the cap is closed, hinders the movement of the engagement means by making the yoke not moveable in a non-engaging position.

In a still further advantageous embodiment means are arranged in the cap for engagement with the housing and limiting the cap's movement with respect to the housing in the cap's open position. Hereby it is assured that the cap, when it is open, can come into a firm position against the housing and thereby constitute a reaction surface. When a person wants to dispense a dose of medication, the device is usually gripped as described above in the hand of the user. This means that one part of the user's hand usually the thump will be placed underneath the device and in this embodiment a surface of the cap will constitute the gripping section, whereas a forefinger will grip and depress the lever arm. It is therefore important that the cap in its open position gives the user a firm grip upon activation. It is therefore in a still further advantageous embodiment of the invention so that the underside of the cap in its open position constitutes a grip and that the grip optionally is ergonomically shaped. The economic shape can be attained by giving the surface in question a saddle-shape. With "saddle-shape" should be understood a surface which curves in two directions so that it will snugly fit into a finger joint, for example in the thumb. Furthermore, the surface of the cap can have a character which gives it non-slip properties, for example by roughening the surface by providing dimples or even by adding a high friction layer to the surface.

In a further advantageous embodiment of the invention, the lever arm is guided by three tracks provided on the inside of the housing where the guidance comprises pins arranged on the lever arm perpendicular to the lever's longitudinal direction and that said pins engage the tracks and preferable identical sets of tracks arranged symmetrically on either side of the lever: a first set of tracks in front of the canister which is generally horizontal; a second set of tracks provided in the yoke also being generally horizontal and a third set of tracks arranged behind the canister and comprising a generally straight upper section and a curved lower section.

In a further advantageous embodiment of the invention, the length of the lever arm is such that when the cap is in its close position and the free end of the lever arm is flush with or contained within the housing and when the cap is in its open position, the free end of the lever arm will project from the housing.

This interaction between the cap and the lever arm does in combination with the above mentioned embodiments of the invention that the device as such has a very user friendly and storage friendly appearance. When the device is closed, there are no projecting members which can become stuck, break or otherwise give rise to unfortunate incidents. In order to activate the device, the user has to do a positive turning of the cap in order to release the engagement means from the cam via activation of the yoke, make the lever arm project from the housing and thereafter grip the device such that part of the users hand will rest on the grip provided by the cap in its open position and thereafter depress the lever arm for dispensing a dose.

In a still further advantageous embodiment of the invention, the lower most section of the yoke and the abutting section of the cam are correspondingly shaped such that a resilient member urging the yoke against the cam will provide a certain resistance against pivotal movement of the cap in its close position. By providing the device with these features, the user will have to make a positive turning of the cap member in order to overcome the resistance forces arising due to the abutting contact between the cam and the yoke. This is further assured by the provision of a resilient member, for example in the shape of a spring which will maintain the yoke in an abutting relationship with the cam in the cap's close position.

The abutting section of the cam can be shaped with a convex or concave section with a corresponding concave or convex section in the end of the yoke such that a positive close position will be felt by the user as these abutting sections engage.

Also during storage and transport of the device, the positive engagement between two abutting sections will minimize the risk of the device accidentally opening.

Dose Counting

An additional problem associated with this type of device is the fact that a canister can contain 100 or more doses of medication. The user will therefore have a tendency to forget how many doses have been dispensed or how many doses are left in the device. This can give rise to severe problems especially if the user is travelling and therefore does not have access to the regular supply of medicaments should the canister run empty.

Furthermore, in certain situations it is desirable to have an indication about when a new canister/device should be bought. For some types of medication it is becoming a legal requirement that an indicating device shall be provided for this type of devices. It is therefore in a still further advantageous embodiment of the invention foreseen that a user is able to see how much is left in the canister by means of a dose dispensing mechanism arranged inside the housing such that a member engaging the rim of the canister will be depressed together with the depression of the lever arm and that said member will transmit the depression to a dose dispenser for registration of a delivered dose and that the dose dispensing mechanism comprises means visible on the housing for indicating the number of dispensed doses or the number of remaining doses.

Either indication i.e. whether it is the number of dispensed doses or the number of remaining doses is interesting information for the user. When indicating the number of dispensed doses it is necessary to know the total number of doses contained in the canister whereas when the dose dispensing mechanism indicates the number of remaining doses, it is necessary to set the dose dispenser when the canister is inserted on the correct number of doses contained in the canister. Alternatively, if it is not desirable to indicate an exact number, the dose dispenser can be arranged to indicate when there is a low dose content in the canister, for example by the lettering "low" or by indicating with a colour code on the readout that only a limited number of doses is available from the canister.

In an embodiment of the invention the dose indicating mechanism is arranged as an integral part of the canister holding means. In this way it is impossible to disengage the indicating means from the canister, whereby errors arising due to inadvertently replacing one canister with another and in this manner perhaps get a wrong content indication can be avoided. Furthermore, the holding means can be provided such that the canister cannot be removed from the holding means.

A dose dispensing device is disclosed, which benefits from the input from the lever arm as described above in that the lever arm causes another large movement/displacement. This displacement makes it easy to detect that an intentional dose has been dispensed or is in the process of being dispensed in that the signal from the lever arm is clear and easily detectable.

In the art there is suggested a number of dose dispensing mechanism, where saw teeth on an indicating wheel are pushed forward by a moveable mechanism, for example in the shape of a secondary lever arm. The secondary lever arm is often activated by the canister's movement and the entire travel length of the secondary lever arm corresponds to the travel length of the canister during the dispensation of a medication dose. There are, however, in the beginning of the movement as well as in the end of the displacement of the secondary lever arm a certain tolerance, which due to the very small displacements of the secondary lever arm in relation to the saw tooth can give rise to inaccuracies in the indication of the number of dispensed doses or, alternatively, the number of remaining doses in the canister. Consequently, there is a need for a dose dispenser, which is more reliable and which operates with tolerances of a magnitude where they are negligible such that reliable information is indicated in the indicating wheels.

Providing for Determined Dispensation and Dose Counting

Due to production tolerances on the canister length and on the fire point, i.e. the exact point in the movement of the input where a dose is dispensed from the canister, it is very difficult to ensure that counting will always happen before the fire point, but never twice within one actuation.

The two following conditions can hardly be fulfilled at the same time:

Count before releasing a dose.

Do not count two doses in one actuation.

One way of solving the problem is to arrange a linear or non-linear gearing element between the canister movement and the input to the dose counter. By doing this, some part of the canister stroke will result in a relatively large input to the counter, while the other part of the canister movement will result in a smaller input to counter. In particular the movement near the fire point can result in a relatively small input to the counter, while the beginning of the stroke can result in a much bigger movement. In this way, the critical tolerances will be less disturbing, since they take up a smaller fraction of the movement.

In other words, the non-linear gearing element will "stretch" the reliable part of the canister movement and "compress" the critical tolerances, thereby enabling the counter to safely display the actual number of doses left in the canister.

This aspect is further improved by the action of the lever arm when the travel of the yoke is larger than the travel of the canister as explained above.

In order to indicate the remaining content or used content in the canister indicating devices comprising one or more wheels can be installed. The indicating devices are often installed such that the user easily can determine the content directly by reading the dial (indicating wheels) arranged behind a transparent section of the housing.

The indicating device may comprise one or more wheels arranged on a common or on separate axles. On the one or more wheels are provided means for engagement with an input arrangement translating the input from the user that a dose is being dispensed into an input that one or more of the indicating wheels shall be moved correspondingly to indicate that one more dose is being dispensed.

In one preferred embodiment two indicator wheels are provided on a common axis. In front of the two indicator wheels, a front cover is provided. In the front cover is provided a window area through which markings on the two wheels can be viewed. On the front is in one example indicated the numbers 1 to 12 and next to each number arranged circumferentially along the periphery of the wheel is arranged a window through which a small segment of the second wheel can be seen. On the second back wheel is circumferentially arranged the numbers 0 to 9 twice. When the front cover and the two wheels are arranged such that the two wheels are arranged around the common axis, it will be possible through the window area on the front cover to see one of the number 0-12 including a window on the front wheel and through that window in the front wheel see one of the number 0-9 on the back wheel. As each dose is dispensed, the back wheel will move onto the next number. The front wheel will be activated to move by means of for example a gear wheel interposed between the two indicator wheels such that the front wheel will be activated to move one notch when the back wheel moves from 9 to 0 or vice versa 0 to 9.

Through the window in the front cover, one or two digits on the front wheel will be visible as well as through the window in the front wheel the numbers on the back wheel will be visible. In this manner it is possible to provide an exact counter of the number of dispensed doses indicating either the number of remaining doses or the number of dispensed doses.

Above the back wheel was described as having the numbers 0 to 9 illustrated twice along the circumference. However, the back wheel can also be numbered from 0 to 9 and therefore only contain ten digits or indicate the numbers 0 to 9 three times and therefore comprise thirty digits or more. The choice depends on how the input is transmitted in order to activate the dispensing device.

The two wheels can also have different diameters such that the front wheel has a smaller diameter than the back wheel whereby it will be possible, without a window in the front wheel, to view the numbers on the back wheel.

Advantages of the Yoke—Dose Counting Means

In an alternative embodiment according to the invention a dose dispenser is disclosed, which dose dispenser comprises indicating means for indicating the available content in the canister, which means comprises two indicating wheels turnably arranged on respective perpendicular axis; a secondary lever arm having means for engaging at least one of the indicating wheels; a pivotable activating member comprising a linear and/or a non-linear section arranged such that the secondary lever arm will abut and slide on said linear and/or non-linear section during a count.

In a further preferred embodiment the linear and/or non-linear section comprises a first curve or a circular section translating into a second curve or linear section translating into a third curve or a circular section.

In this manner a count, i.e. registration and indication of a dispensed dose, comprises three distinct movements by the secondary lever arm engaging the indicating wheels. The first movement is caused by the protrusion sliding along a first curve/circular section. By this movement the protrusion on the lever arm engaging the indicating wheel is brought into engagement with engagement means arranged on the indicating wheel. Hereby any slack and tolerances in the system is taken out and the dispense mechanism is prepared for the count. The count is activated by the protrusion sliding along the second, preferably linear, surface on the lever arm. As the lever arm has engaged and taken up any slack in the system between the indicating wheel and the lever arm, the lever arm will be depressed and thereby the indicating wheel will be turned/rotated due to the sliding movement along the second surface. As the second surface translates into the third curved, circular shaped surface the lever arm will not move any further thus allowing the canister to be fully activated. In this manner a definite input is created by depressing the lever arm in order to activate the mechanism such that one dose is being registered in the indicating wheels.

In a further embodiment the pivotably fastened lever arm has an engagement point which engages a translating yoke, which yoke comprises a projecting member which is adapted to engage a secondary lever arm having means for translating the movement of the projecting member to a dose counting mechanism, where the engagement point engages the yoke on an upper surface of said yoke.

By transferring the movement of the lever to the yoke, a rather long travel of the active parts is achieved, whereby better accuracy relating to the firing point may be achieved.

In a still further embodiment, wherein the lever arm's movement is transferred to the yoke, the upper surface of the yoke is linear, such that the engagement point transfers the movement of the pivotably mounted lever in a linear movement to the yoke.

In this embodiment the user will feel a smooth and constant movement of the lever as the engagement point slides along the linear top surface of the yoke.

In an alternative embodiment of the engagement point/yoke the upper surface of the yoke is divided into two or more distinct linear sections, where the lever arms engagement points' travel along the second section creates a substantial part of the yoke's downward movement.

In this particular embodiment the lever arm's movement may be constant whereas the yoke will travel downwards in different tempi, depending on the linear sections arranged at the top of the yoke. In a particular desired configuration, the first section is arranged such that the engagement point during its travel along this first section only will depress the yoke very slightly. The yoke's movement may be compared to an initial movement taking up slack and tolerances in the device.

The second section may be very steep in relation to the engagement point's travel, whereby a rather large depression of the yoke occurs in comparison to the movement of the lever, and finally in a third section the yoke's movement again in relation to the engagement point may be negligible as the movement is used to finish the movement or action by the lever.

In a further advantageous embodiment of the invention a part activated by the lever arm comprises engagement means for engaging the indicating wheels. The indicating wheels can be supplied with a groove which is arranged in a circular surface of at least one of the wheels at a distance from the rim. The groove comprises spaced radial sections connected with curved or linear sections. In a further embodiment said groove may for example comprise interconnecting and alternating radial and peripheral sections arranged such that a part of the lever arm is inserted and slidably arranged in said groove and further that means for urging at least one wheel to rotate is provided. The groove may also be shaped as a saw tooth track, wherein radial sections are interconnected with linear or curved sections (corresponding to the peripheral sections) alternating at either end of the radial section. Also, other patterns or designs of the groove can be contemplated within the principle of the rotation of the wheel being hampered by engagement means on a secondary lever arm engaging notches or the like (radial sections) on the wheel.

The groove will be a guidance track for the secondary lever arm's movement. If the secondary lever arm encounters a radial section, the wheel will not be able to rotate further. By moving the secondary lever arm in a radial direction, i.e. depressing the canister and dispensing a dose, the dispensing wheel will be released from its engagement with the secondary lever arm and be able to rotate. The length of the rotation is determined by the length of the peripheral groove section. This length should correspond to the indication of one dispensed dose. By furthermore providing means for urging the wheels to rotate, for example in the shape of a pre-stressed spring or similar device, the side of the groove will always be in contact with the part of the secondary lever arm engaging the groove. By the next radial movement of the secondary lever arm the wheel will again be released and be able to rotate the equivalent of a peripheral section's length.

This embodiment is especially advantageous in that the dispensing mechanism does only require the absorption of small and negligible tolerances in that the formation of the groove will dictate the movement of the indicating wheel.

In a further advantageous embodiment the peripheral sections of the groove have different and increasing lengths along the periphery of the wheel. Hereby it becomes possible to have an unlinear indication on the indicating wheel. This is especially advantageous in that when the device is new and unused the user is certain that a large number of doses is available. The interesting question to a user is, especially when a large number of doses have been dispensed, how many doses are left in the canister. It can therefore be advantageous to have an exact and clear indication of the number of doses remaining in the canister when there is only a low number of doses left. This can be provided by having very short peripheral sections on the indicating wheel in the area with a large number of doses left in the canister and relatively longer sections when there are only a few doses left in the canister. Hereby is facilitated that the movement of the wheel is larger and thereby the indication clearer.

In a further advantageous embodiment the interconnected and alternating radial and peripheral sections are arranged in a spiral on the surface of the at least one wheel. In this configuration it is possible to have an unlinear indication with a large number of doses, whereby the indicating wheel will do more than one revolution in order to indicate the number of doses dispensed.

The invention furthermore comprises a method for counting dispensed doses from a device as described above, wherein by depressing the lever arm which thereby rotates around the fastening point of the lever arm in the housing, the protrusion comprising a first curve or circular section translating into a second curve or linear section translating into a third curve or linear sections slides on a secondary lever arm such that the secondary lever arm has an end part which engages means on at least one of two indicating wheels arranged on a mutually perpendicular rotating axis such that the downward movement of the secondary lever arm creates a rotation on at least one indicator wheel.

In a further preferred embodiment of the invention, at least part of the device for example the housing, the cap and/or the lever arm is coloured or otherwise marked according to a predefined code representing a specific drug contained in the canister. This embodiment is especially useful for patients which suffer from different diseases at the same time which require different medication. Also patients requiring different concentrations of their medicament at different times, for example a higher concentration before going to sleep, would also easier be able to determine the correct device to use in any given situation.

By having a specific colour for the medication suitable for treatment for one disease or in a given time, the user will be able to recognise and use the correct device according to the symptoms.

In some of the embodiments of the present invention, the canister is completely enclosed within the device whereby it is impossible for the user to read information which may be printed on the outside of the canister. This information can also be provided on the device, but as an additional safety caution, a distinctive colour coding should also be provided. This is due to the fact that in acute cases, the user having more than one device should not have any doubt as to which one to use according to the situation and as there furthermore is usually a high level of stress in these situations paired with perhaps reading impairment requiring glasses it does provide an additional safety aspect to distinctively colour code the device itself.

Return Blocking Function

Often these types of devices comprise a dose counter such that the patient will be able to keep track of how many doses are left in the device such that a new device or canister can be provided in due time. It is therefore important that when the patient dispenses a dose, only one dose is dispensed and at the same time only one dose is counted.

Due to inherent tolerances in production in order to keep production costs of these types of devices as low as possible, and furthermore as a consequence of the play arising from a number of mutually cooperating parts, it is sometimes possible to activate the bottom either from the non-depressed state or from the semi-depressed state, whereby the dose counter may be activated without an actual dose being dispensed or a dose may be dispensed without activating the dose counter.

For this type of device as for many other types of devices it is undesirable that depression of a button/lever, which is intended to effect a function, i.e. initiate an event, where said function may have more than one result, i.e. the example mentioned above, the activation of the button shall result in the dispensation of a dose and at the same time counting/registration of said dose. It is paramount that both these events happening by depressing the bottom are reliable registered and carried out without the possibility of unintended or intended tampering with the device.

Consequently, the present invention provides a mechanical return blocking device comprising two cooperating and mutually displaceable parts:
  a first part wherein parallel to a longitudinal axis at least one set of tracks comprising a first track and a second track is provided, and that the second track comprises one or more retaining members and a sliding guide arranged at one end of the second track;
  a second cooperating part wherein a leg member comprising an engagement section for engagement with the tracks provided on the first part is provided, and that said leg member is biased towards the first part and that the engagement section is adapted to travel in the direction of the longitudinal axis;

and further that the retaining members allows the engagement section of the leg member to move in a first direction towards the sliding guide but blocks movement in the opposite second direction and that the engagement section of the leg member slides on the sliding guide, whereby the engagement section and thereby the leg member is directed from the second track to the first track.

The device thereby provides a first track where the engagement means can travel unhindered in one direction. When built into a device where it is desirable to have a complete button stroke, the engagement section will slide on the first track completely unhindered. During movement in the first direction the engagement section of the leg member will abut the side of the second track made up of one or more retaining members due to the biasing force applied to the engagement section. Once the engagement section reaches the bottom of the intended travelling stroke corresponding to a stroke of the button/lever, the biasing force will push the engagement section onto the second track and the engagement section will move in a second direction towards its starting position and thereby pass the one or more retaining members.

Should a user during the movement in the second direction of the engagement means alter the direction, i.e. try to depress the button/lever again, the engagement section will engage the retaining members, whereby relative movement of the two cooperating parts will be impossible.

Should a user during the depression of a button corresponding to the engagement section moving in the first track change direction, i.e. from first to second direction, such that the engagement section begins a movement in the opposite direction, the biasing force will urge the engagement section onto the second track such that further forward movement will be hindered by the engagement section's position in the second track where one or more retaining members are provided, whereby further movement in the first direction is impossible.

In order to again move the engagement section in the first direction corresponding to pushing/activating the button or lever again, the engagement section must have been returned and the engagement section must have been brought into contact with the sliding guide, whereby the engagement section during a further forward movement again will slide in the first track abutting the retaining members on the way to completing an activation of the event by the button/lever.

In this manner by designing the one or more retaining members in such a way that the event which should be triggered by activating the button/lever will only take place once one or more of the retaining members have been passed in the first direction, it can be assured that a reliable action when depressing the button/lever is facilitated. If a depression of the button/lever is disengaged during the travel, the engagement section as described above will be forced into the second track and will by further movement in the first direction engage the retaining members making travelling in that direction impossible.

Therefore by arranging retaining members correctly, play in the device and tolerances can be counteracted, whereas a movement of the button/lever for activation or initiating of the event will reliably be carried out by the device. Tolerances and play in the device are therefore assimilated by the initial movement of the engagement section in the first track and once it enters the activation zone, it is due to the construction of the device impossible to turn back and reactivate without a complete return to the starting position. This in turn means that the activation should be provided for by a relatively short movement of the button/lever.

In a further advantageous embodiment each retaining member comprises an inclined sliding surface having a predetermined length along which the engagement section will slide, and a step in the shape of a surface arranged at a sharp angle in relation to the sliding surface, said step connecting the top of one inclined sliding surface and the bottom of the next sliding surface, such that a saw-tooth configuration is created, and such that the engagement section of the leg will be retained from movement in one direction by said step.

This configuration is relatively simple to produce and further the construction can be made such that a user will feel the teeth of the saw tooth structure indicating that the button is in its return movement. When constructing the device itself it is relatively simple to design the length of the sliding surface such that it will be designed exactly for the desired movement of the button/lever.

The formulation "step in the shape of a surface arranged at a sharp angle in relation to the sliding surface" shall in this context and within the application be understood as a surface at such an angle that the engagement section of the leg member travelling up the inclined sliding surface, will fall down and be retained by this step, which thereby hinders the movement in one direction and therefore only allows the engagement section to travel up the adjacent sliding surface if such is provided.

In a further advantageous embodiment at least a part of a side surface facing the first track of each retaining member is arranged at a shallow angle in respect to the longitudinal axis of the device, such that the inclined sliding surface is narrowest in the end of the first travelling direction of the engagement section.

In this embodiment it is provided that the side surface of the second track, against which the engagement means abuts by movement in the first direction, is made such that the engagement means will not become stuck due to unevenness or the like in that by arranging the side of the retaining member at a shallow angle, the engagement member which abuts this side will continuously be pushed outwards during its movement in the track.

In a further advantageous embodiment the inclined sliding surface overlaps an adjacent inclined sliding surface, and the inclined sliding surface tapers perpendicular to the longitudinal axis such that the top is narrower than the bottom of the sliding surface, whereby the step at the bottom is narrower than the adjacent sliding surface at their connection point.

By this construction a wedge-shaped part of the inclined sliding surface is exposed next to the adjacent retaining means. During the reverse movement where the engagement section moves into engagement with the retaining means, the wedge-shaped section exposed by the taping side section facilitates the engagement sections travel into the retaining means.

In a still further advantageous embodiment the leg member is pivotally fastened in the end opposite the engagement section, and that the first part comprising the at least one set of tracks has a corresponding circular configuration arranged at a distance, whereby the engagement section may engage the tracks.

It is obvious that the device described above will function where the relative movements between the first and second parts are linear. It is however also contemplated within the scope of the invention that the leg member can be pivotally fastened such that the engagement section will perform a movement corresponding to a partly circular movement. In order to contain the retaining means at a distance from the engagement section of the leg, the retaining means may also be arranged on a circular shaped member, where the radius of the circle corresponds to the distance between the pivotal fastening point of the leg member and the engagement section's outer tip. By this arrangement it is assured that when the activation of the lever or button translating the action to the leg, the engagement section of the leg will stay in abutting contact with the two tracks arranged on the first part. In this manner the same advantages are achieved as described above.

In a further embodiment the width of the sliding guide perpendicular to the longitudinal axis at its widest section is at least as wide as the retaining members step.

By incorporating the mechanical return blocking device into devices of this type and designing the size and distribution of the retaining members according to the use, it can be achieved that once a user activates the button or lever and moves it past the activation point, a dose is dispensed and also optionally a dose counting device is activated without the user being able to change direction. A change of direction necessitates that the button/lever is brought back to its initial starting position before a new stroke may be commenced.

In a further advantageous embodiment of the device the mutually displaceable parts are formed as integral parts of the device, such that the first or second part is integral with part of the button arrangement and the other part is integral with a non moving part of the device.

This manner of production facilitates that the inventive advantages of the device are provided at very low costs in that the parts of the device can be moulded from the out-set with the two parts necessary in order to create the mechanical blocking device. Furthermore in cases where the device is injection moulded, it is a very simple and thereby cheap process to manufacture these added advantages into the device itself in that only the injection moulding tool has to be modified.

In a further advantageous embodiment the mechanical return blocking device is especially designed such that play and tolerances arising in the device from production, assembly and manufacturing circumstances are compensated by shaping and designing the engagement sections' travel between at least two adjacent retaining means or the retaining means and the sliding guide corresponds to the activation of one event, where an event may be the dispensation of a medicament dose and/or the input for a dose counting device.

By designing the device such that the event will take place only after the engagement section has past the last retaining means in the first track, it can be assured that depression of the button/lever either will not be completed and therefore the dose dispensation and dose counting will not be activated, or the button/lever is depressed all the way past the activation point or points in one movement assuring the correct dispensation and counting of a medicament dose.

For some applications it will be desirable to produce the canister, the dose indicating activating means and the dose indicating means as one integral unit which cannot be disassembled without destroying one of the components. The unit can advantageously comprise a part of the surface section of the housing. By this arrangement, the medication corresponding to the colour code of the section of the housing has not been replaced, altered or in any other way tampered with such that the user can be assured that the medication in the canister corresponds with the colour code and, furthermore, that the amount or number of indicated doses in the dose indicating device corresponds to the amount or number of doses in the canister.

In the inventive embodiments of the invention as described above, the inhaler has been described as comprising among other inventive features a yoke and a return blocking device. It should in this context be noted, however, that the principle of transforming the input from the lever arm to the dose counter via the linear or non-linear configuration of the interface between the lever arm and the yoke or the yoke and the input means for the dose counter makes it possible, due to the increased movement of the lever arm in relation to the movement of the canister, to compensate for play and tolerances and also create/design a determined firing action. Likewise, the same applies to the return blocking device. The configuration/principle of assuring that the movement is completed in one action may also be used separately in other types of devices where such a feature may be desired.

BRIEF DESCRIPTION OF THE DRAWING

The invention will now be explained in more detail with reference to the accompanying drawing. It should be noted however that the invention is not limited to the specific embodiments as described above, but is only limited by the scope of the appended claims.

In the drawing

FIG. 17 illustrates a cross-section of the device, FIG. 18 illustrates a cross-section of an alternative embodiment of the device illustrated in FIG. 17, FIG. 19 illustrates a mechanical return blocking arrangement, FIG. 20 illustrates the central parts of the mechanical return blocking device.

DETAILED DESCRIPTION OF THE PREFERRED EMBODIMENTS

The same elements will be given the same reference numbers in all drawings.

The present invention is explained with reference to a canister containing the medication and a propellant. The canister comprises a bottom, cylindrical sides and a top. The top comprises a rim where the cylindrical sides are assembled or merge with the top. In the top is arranged a nozzle for dispensing the medication.

Inside the canister in immediate connection with the nozzle is arranged a valve wherein the actual measuring of each dose to be dispensed takes place.

Figure 4:
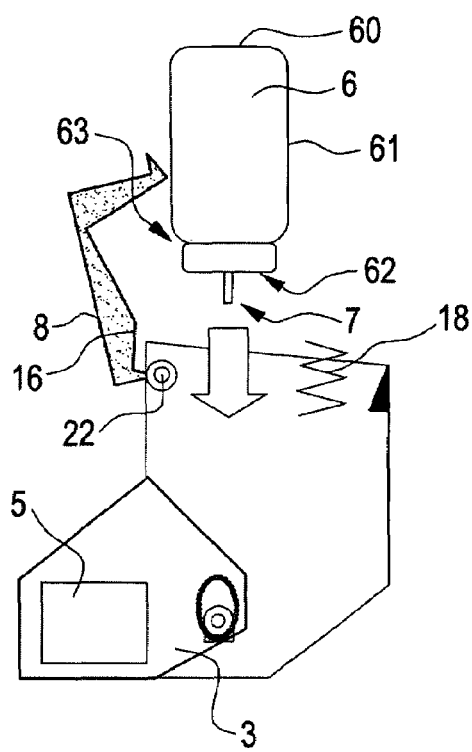

As schematically illustrated in FIG. 4, the canister 6 comprises a bottom 60 and cylindrical sides 61. Where the top 62 is joined with the sides 61, a rim 63 is formed. The nozzle is indicated by 7.

Figure 1:
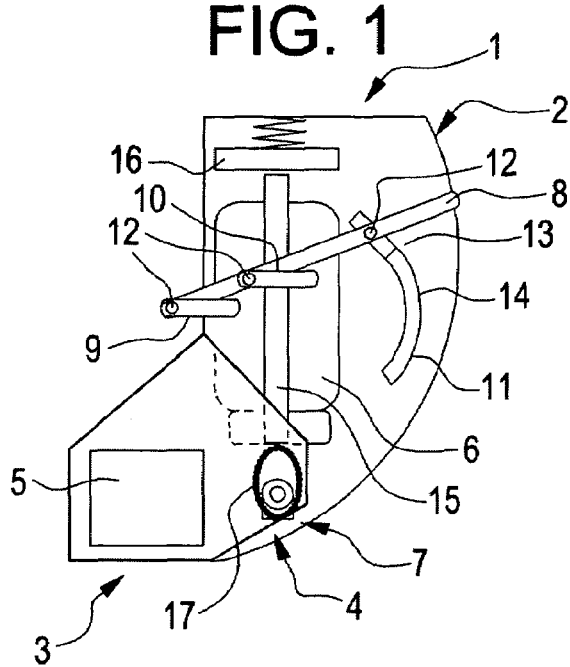
FIG. 1-3 illustrates a schematic first embodiment of the device in a closed, open and activated position, In FIG. 4, 5 and 6 a second embodiment of the invention is illustrated.

FIG. 1 is a principle sketch of how the device in one embodiment of the invention can be mechanically constructed. The device 1 comprises a housing 2, a cap 3 pivotally connected to the housing by a hinge-like construction 4. Covered by the cap 3 is a mouthpiece 5 through which the medication contained in the canister 6 having nozzle means 7 can be dispensed.

In the figures the canister 6 is shown in an upside down position which is to be understood that the nozzle means 7 of the canister are pointing downwards.

A lever arm 8 is provided for reducing the force needed to press the canister 6 against the seat 59 such that a medication dose will be dispensed.

The lever action in this embodiment is guided by three tracks 9, 10, 11 arranged in the housing. In order to guide the lever 8 in the tracks 9, 10, 11 pins 12 are provided perpendicular to the lever for guidance in the tracks 9, 10, 11. In the closed position as illustrated in FIG. 1 the cap 3 completely hides the mouthpiece 5. In this position no part of the lever arm projects outside the housing 2. For illustration purposes, the lever arm 8 in FIG. 1 has been indicated as projecting outside the housing, but in the actual device the track 9 will be comprised inside the housing and partly covered by the cap 3. Likewise the free end i.e. the end of the lever arm not connected with pins to a track is also completely flush with the device. As can be seen from FIG. 1, the two tracks 9 and 10 are substantially horizontal. The third track 11 comprises a linear section 13 and a curved section 14. The track 10 is provided on a yoke-mechanism 15 connected to the lever arm. The yoke-mechanism 15 comprises means 16 for engaging the bottom of the canister 6.

Inside the cap 3 a cam 17 is provided in connection with the hinge-like 4 connection between the cap and the housing. The cam 17 and the bottom of the yoke 18 are in abutting relationship when the cap is closed such that the means 16 for engaging the bottom of the canister cannot exert any pressure on the bottom of the canister and thereby inadvertently dispense a dose into the cap.

Figure 2:
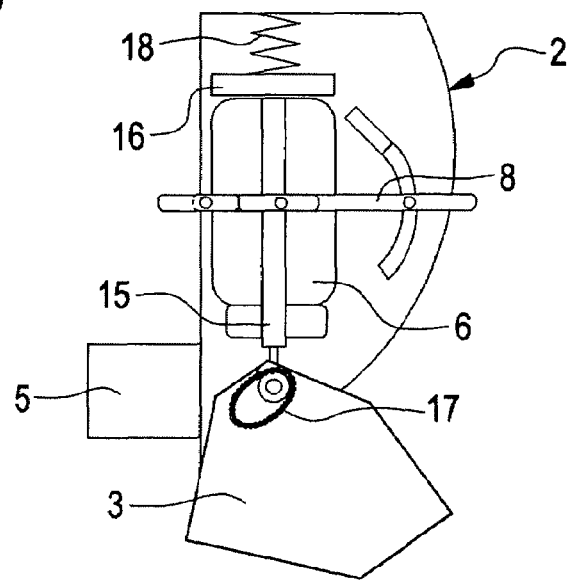

When opening the cap as illustrated in FIG. 2 access is gained to the mouthpiece 5. At the same time the yoke 15 is released from its abutting relationship with the cam 17 and due to the very low pressure caused by the spring member 18, the means 16 for engaging the bottom of the canister 6 are moved into a position where the means 16 very lightly touches the canister 6. The cap no longer abuts the top of the pressurized canister or the means for engagement with the bottom end of the pressurized canister when the cap is in its open position.

At the same time the lever arm 8 is moved downwards because of the yoke's 15 downward movement due to the pressure from the spring 18 such that part of the lever arm 8 will project from the housing 2. This movement is guided by the three tracks 9, 10, 11 wherein the pins 12 can slide in respect of the movement caused by the lever arm.

Figure 3:
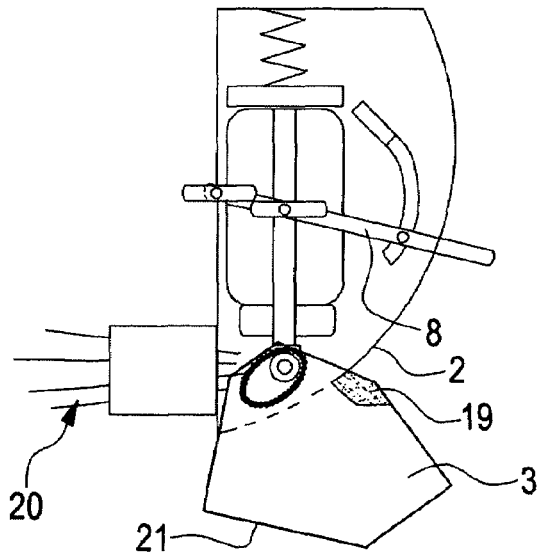

In FIG. 3 the cap is in its completely open position whereby means 19 having engaged the housing 2 and in this way blocked further movement by the cap 3 in relation to the housing 2. The lever arm 8 can now easily be depressed whereby a dose 20 can be ejected through the mouthpiece and into the respiratory system of a user. When the lever arm is released after the dose has been dispensed, the resiliency built into the nozzle section of the canister will force the canister upwards into a position as illustrated in FIG. 2. For this embodiment of the invention to work, it is very important that the resilient member 18 is weaker than the means built into the canister for resetting into the closed position as illustrated in FIG. 2. The spring member 18 only serves to depress the yoke and thereby the engagement means 16 into abutting contact with the canister 6 whereby the lever arm is moved from a stored position flush with the housing to an exposed position where a part of the lever arm projects from the housing as illustrated in FIG. 2. The movement of the lever arm from the position as indicated in FIG. 2 to the position indicated in FIG. 3 where a dose is disposed is done manually by the user by griping the device, for example with the thumb on an abutment surface 21 on the cap and a forefinger on the projecting section of the lever arm 8 and forcing the lever arm downwards.

Figure 5:
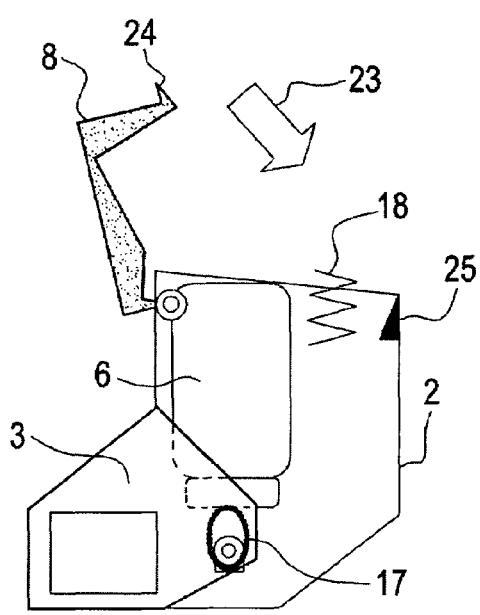
Figure 6:
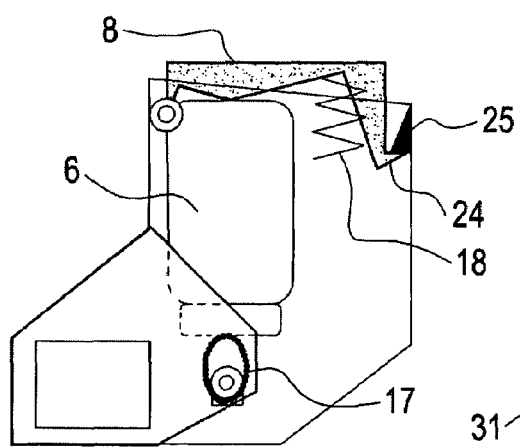

In FIG. 4-6 is illustrated how a canister is inserted into an embodiment of the invention. In FIG. 4 the device 1 is in its canister-receiving position. In this position the integrated means 16 for engagement of the bottom of the canister and the lever arm 8 are opened by pivoting the lever arm around the pivotal connection 22. Hereby access is created to the interior of the device 1. The cap 3 is closed and the mouthpiece 5 is thereby covered.

In FIG. 5 the canister 6 is inserted into the housing 2 until it comes into abutting contact with the cam 17 on the cap 3. It is thereby impossible to insert the canister further into the housing. Thereafter the lever arm 8 is pivoted as indicated by the arrow 23. The lever arm in its free end, i.e. the end which is not fastened to the pivotal connection 22, is supplied with a hook section 24. A corresponding grip section 25 is provided on the housing 2 such that when the lever arm is pivoted into a closed position as illustrated in FIG. 6 the hook section 24 will abut the grip section 25 such that the lever arm 8 by depression can move downwards but upwards movement is hindered by the hook and grip sections 24, 25. A spring-member 18 can be provided which spring-member 18 abuts the lever arm 8 such that the hook section 24 when not depressed is kept in contact with the grip section 25.

In order for the user to dispense a dose form the canister 6, it is necessary to pivot the cap 3 into its open position as illustrated in FIG. 3 whereby the cam 17 comes out of its abutting relationship with the top of the canister 6. By depressing the lever arm 8, the nozzle of the canister 6 will dispense a dose.

In the two embodiments illustrated above access for the user to the canister is hindered either because of the closed nature of the housing 2 as illustrated in FIG. 1-3 or by the hook and grip sections illustrated in FIGS. 4, 5 and 6. The snap-joint created by the hook section 24 and the grip section 25 effectively avoids unintended access to the interior of the housing and thereby to the canister by a user. On the other hand, the snap-joint provides for the possibility of manufacturing the device in a place different from the mounting of the canister into the device such that devices can be produced in one place, canisters in a second place and the whole assembly of the device and canister can take place in a third location. The snap-joint furthermore prevents a user from removing a canister from the device. Hereby is avoided that the colour-coding or other means of indicating what kind of medication is contained within the housing does not correspond to the canister actually is comprised in said housing.

Figure 7:
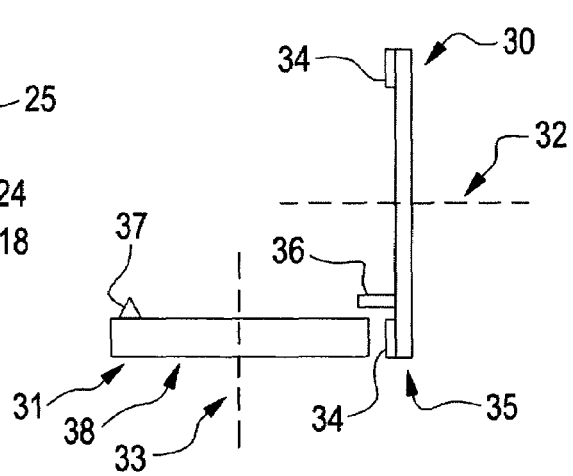
FIG. 7 illustrates a schematic construction of the dose indicator wheel arrangement.

In FIG. 7 two indicator wheels 30,31 are indicated arranged on mutually perpendicular rotating axis 32,33. The first indicator wheel 30 has means for engagement 34 arranged such that the indicator engagement means provided for example by a second lever arm can rotate the indicator wheel 30 one step at a time. The indicator wheel 30 can be equipped with numbers or other means for indicating the number of doses left in the canister. This indication would be arranged on the rim 35 of the wheel. As the indicating wheel 30 is rotated around the axis 32, the means 36 will per revolution push the second indicating wheel 31 one step. This is caused by the engagement means 37.

The indicator wheel 31 will have its dose indicating numbers or colours on a front surface 38 of the wheel 31. As the wheel 30 rotates, the numbers from 0 to 9 could for example be indicated on the rim 35. As the engagement means 36 engages the engagement means 37 provided on the second indicator wheel 31, this will cause movement of one notch on the indicator wheel 31. By providing the second indicator wheel 31 with the number 1 to the number of doses in a canister divided by 10, it becomes possible to indicate exactly the number of doses dispensed or alternatively the number of doses left in the canister. This is due to the fact that the engagement means 36 will push the engagement means 37 one notch and thereby add or subtract a factor 10 from the indicating means provided on the surface 38 of the indicator wheel 31.

Figure 8:
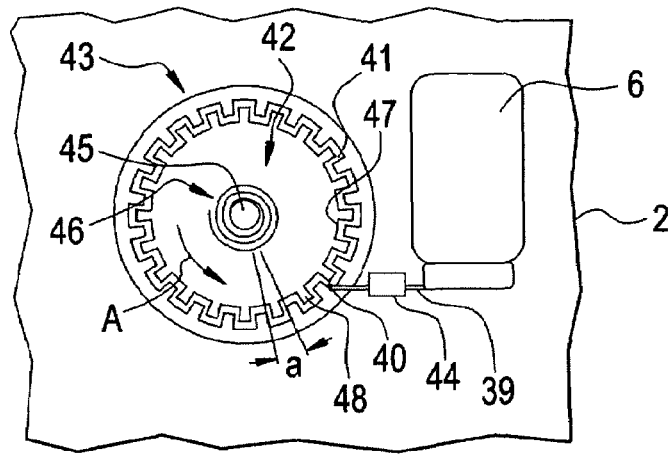
FIG. 8 illustrates a schematic dispensing device.

Turning now to FIG. 8, alternative means for registering and indicating the dispensation of a dose is indicated. The canister 6 is hereby schematically arranged in contact with a lever arm 39. The lever arm has an end part 40 which engages a groove provided in a surface 42 of an indicating wheel 43.

By depressing the canister 6 translation of the downward movement by the means here schematically indicated as a box 44 will translate this movement into a movement of the end of the secondary lever arm 40 such that the end of the lever arm will move gradually towards the centre 45 of the indicator wheel 43. Due to the means 46 provided for urging the indicating wheel 43 to rotate in the direction indicated by the arrow A, the peripheral section 47 of the groove 41 will move past the end of the lever arm 40 until the radial section 48 of the groove engages the end of the lever arm 40 and thereby stops further rotation. By arranging suitable indication means on the indicating wheel 43 the rotation of the indicating wheel 43 can correspond to indicating one dose dispensed.

By varying the length a of the peripheral sections, it will be possible to have an unlinear representation of the number of doses dispensed.

Figure 10:
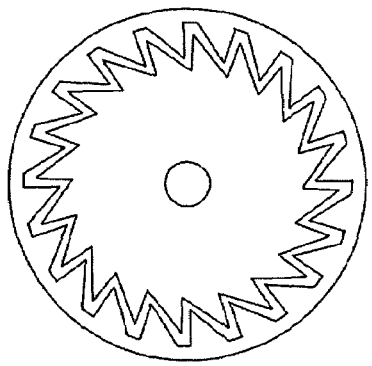
FIG. 10 illustrates an alternative groove configuration.
Figure 11:
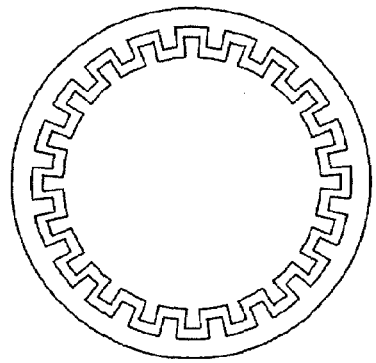
FIG. 11 illustrates an alternative groove configuration.

In FIGS. 10 and 11 alternative configurations of the groove are illustrated. The main principle of the groove is the provision of radial sections or notches interconnected with groove sections allowing the end of the secondary lever arm to be stopped by the radial sections and the wheel to rotate through the interconnecting groove sections.

Figure 9:
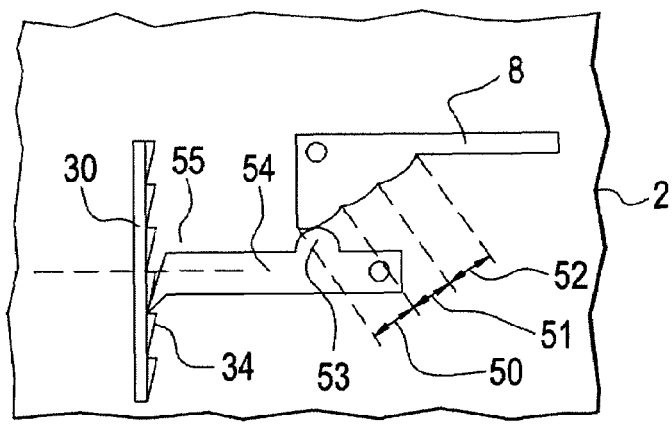
FIG. 9 illustrates a schematic lever arm arrangement.

In FIG. 9 an alternative embodiment for activating the dose indicating means is illustrated. A mechanism for activating the secondary lever arm engaging the indicating wheel is illustrated. The lever arm 8 being the same lever arm as described above with respect to the embodiments illustrated in FIGS. 1-6 is equipped with a protrusion consisting of three distinct sections. A first section 50 being in the shape of a curve or circular translating into a second section 51 preferably curved shaped or linear translating into a third section 52 being curved or circular in shape. These sections engage a protrusion 53 provided on a secondary lever arm 54 such that depression of the secondary lever arm will occur in three distinct movements. Firstly by engaging the first section 50 any slack between the end of the lever arm 55 and means arranged on an indicating wheel 34 will be absorbed. As the protrusion 53 slides on the second surface 51, the actual depression and thereby movement of the indicating wheel 30 will occur. As the lever arm 8 is further depressed, the protrusion 53 will slide on the surface 52 whereby the pressure created by the end of the lever on 55 on the means for engagement 34 will lessen and the rotational movement of the indicator wheel 30 will subside. Hereafter the dose is completely dispensed and the user will release the lever arm 8, whereby it will be pushed back into its original position by the spring member 18 and at the same time release the end of the lever arm's 55 engagement with the means 34 such that the lever arm 54 can move back into the position indicated in FIG. 9.

The box indicated in FIG. 8 by reference number 44 can be constructed in a similar fashion as illustrated schematically in FIG. 9.

Figure 12:
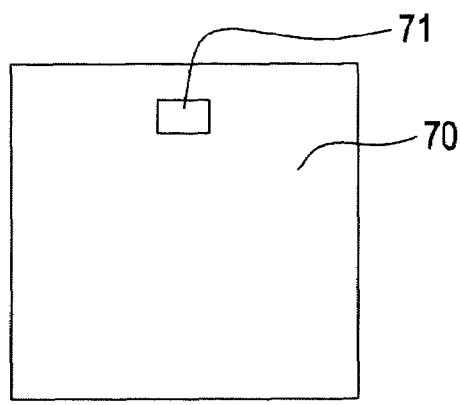
FIGS. 12-16 illustrate different embodiments of the dose indication means.
Figure 13:
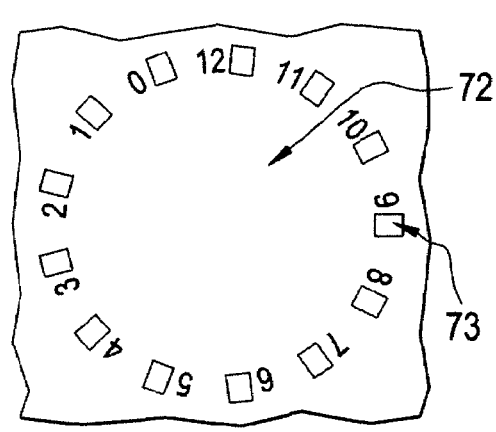

In FIGS. 12-16, an alternative embodiment of the indicating means is illustrated. FIG. 12 illustrates a front cover 70 comprising a window area 71. FIG. 13 illustrates a front wheel 72 on which the numbers 0-12 have been arranged on a peripheral section along the periphery of the wheel. Next to each number is a window 73 provided.

It should, however, be noted that rollers provided with numbers may readily be arranged instead of the wheels used in this particular embodiment.

Figure 14:
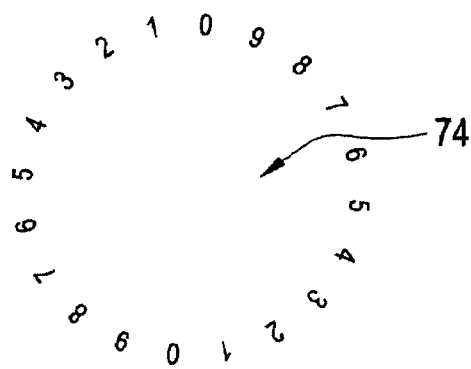

In FIG. 14 a back wheel 74 is illustrated. Along the periphery of the wheel, the numbers 0-9 are provided twice. By superposing the two wheels and the front cover, it will be possible to view the numbers through the window 71 in the front cover such that the numbers on the front wheel 72 as well as the numbers provided on the back wheel 74 will be visible through the window 73 such that the actual number, i.e. the combination of the number on the front wheel 72 and the number on the back wheel 74 will be visible through the window 71.

Figure 15:
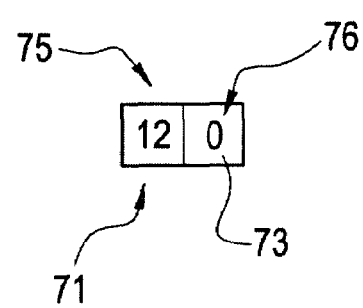

In FIG. 15 the window 71 is illustrated, wherein the numbers on the front wheel 72 are visible along with the window 73 provided in the front wheel such that the numbers 76 on the back wheel 74 are visible through the window 71 in the front cover and the window 73 in the first disk becomes visible. In the illustrated example "120" doses are remaining in the canister.

Naturally, the disks can be arranged to count upwards or downwards, depending on choice. Likewise, the numbers can be given any suitable colour or different colours.

Figure 16:
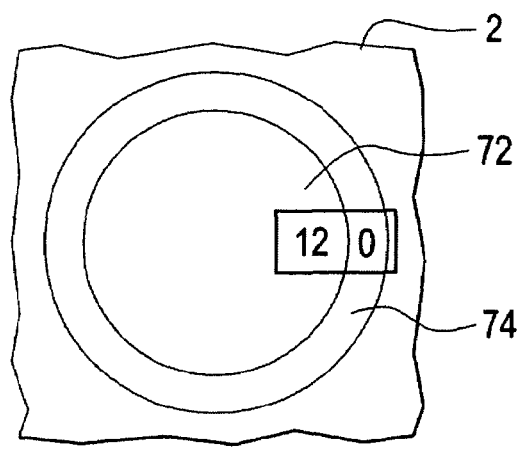

In FIG. 16 is illustrated a special embodiment where the front wheel 72 has a smaller radius than the back wheel 74.

A method of assembling the device may comprise the following steps:

the cap means are brought into its closed position, and if an access lid is provided in the top of the housing for allowing access through an opening to the interior of the housing this lid is removed from said opening;

the pivotal engagement means are pivoted away from the housing, thereby allowing access to canister receiving means arranged inside the housing, where the canister receiving means comprises a seat means for receiving the top end of a canister, and means for guiding the canister inside the housing;

a canister is inserted into the housing with its top down i.e. its ejecting nozzle first, such that the top nozzle of the canister engages the seat;

optionally a spring member is arranged on a spring seat or the engagement section, said spring members free end projecting upwards;

the engagement means and optionally the lever arm is pivoted into abutting contact with the bottom of the canister, optionally compressing the spring member, and thereby either engages a snap joint or where a lid is provided, the lid optionally compressing the spring member is replaced on the housing.

In FIG. 17 is illustrated a cross-section through an inhalation device 1. The lever 77 is formed with an integral engagement point 78, which engagement point engages a translating yoke 79 on a top surface of said translating yoke. The translating yoke is connected to a secondary lever 80, which will create input for the dose counting device (not illustrated). By configuring the top surface 81 of the translating yoke 79 in a particular manner, the input movement from the lever 77 can be transformed to any desired input via the secondary lever 80.

In the configuration illustrated in FIG. 17 the entire top surface 81 of the translating yoke 79 is linear having a constant pitch. Therefore, when activating the lever 77 to pivot about the pivot point 82, the lever will perform the movement as indicated by the arrow 83 into the position corresponding to the lowermost point of the stroke illustrated by dashed lines 84.

Turning to FIG. 18 a corresponding device is illustrated, but the top surface 81 of the translating yoke has been divided into three separate linear sections 85, 86, 87. As the engagement point 78 travels along the first section 87 due to rotation of the lever 77 about the pivot point 82, the translating yoke 79 will only perform a very slight downward movement.

As the engagement point 79 engages the steeper second section 86, a substantial part of the translating yoke's downward movement will be performed as the engagement point 78 travels along section 86. As the engagement point 78 engages the third surface 85, the translating yoke will again only perform a very slight movement due to the almost horizontal travel of the engagement point in relation to the third surface 85.

In this particular configuration the first section 87 may be used to absorb slack and tolerances built into the device, such that when activating the device in order to dispense a dose, i.e. passing the fire point, a determined movement by the secondary lever arm 80 will be accomplished due to the fact that any slack and tolerances already are absorbed by the engagement point's travel along the first section 87.

The device may further be provided with a mechanical return blocking arrangement, as illustrated in FIG. 19.

A typical inhalation device comprises a mouthpiece 88, an activating button 89, above reference is made to a lever arm 8,77, a canister 90 comprising the medication to be dispensed through the mouthpiece 88. This and other embodiments of the invention have been explained above. By depressing the button 89, the canister 90 will be forced downwards and via a valve device 91 a dose will be dispensed through the mouthpiece. In the embodiment described with reference to FIGS. 19-23, a mechanical return blocking device is arranged such that a leg 92 is integrated in the button 89 (or lever arm). The return blocking device comprises two parts; A first part 95 and a second part 92 which by interaction create the return blocking device. The button 89 is designed to pivot about the pivot point 93. By the movement of the engagement section 94 of the second part will abut the first part 95 which is integral with the inhalation device.

In FIG. 20 is illustrated two cooperating parts making up the central parts of the mechanical return blocking device. A first part 95 and a second part 92. The two parts 95,92 are intended to be mutually displaceable such that the first part 95 will be able to slide in relation to the second part 92.

Which part slides in relation to which other part does not influence the proper workings of the device.

Figure 21:
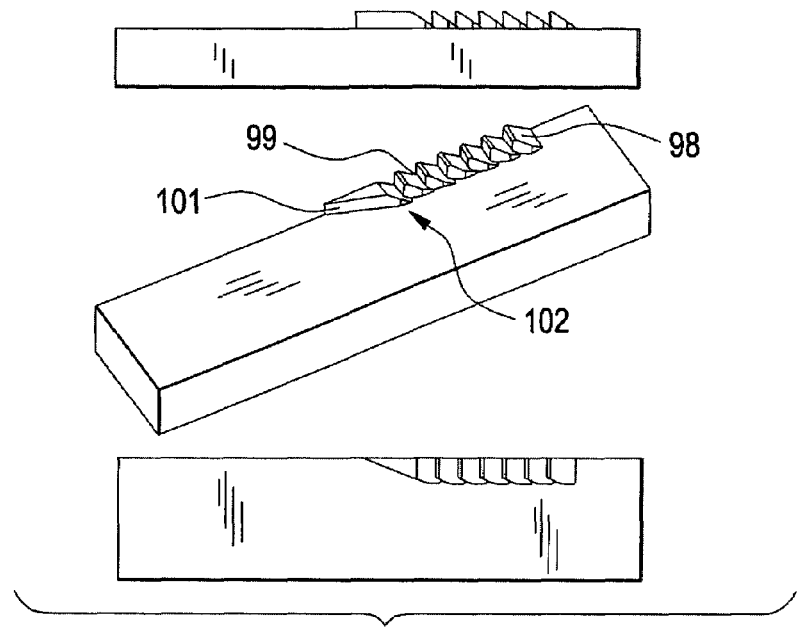
FIG. 21 illustrates a sliding guide.

On the first part 95 is provided a number of retaining means 97, where each retaining means in the illustrated embodiment comprises an inclined sliding surface 98, which is connected with a step 99, see FIG. 21. The step connects the top of one inclined surface 98 with the bottom of an adjacent inclined surface arranged on an adjacent retaining means. The retaining means is furthermore provided with a tapered surface 100.

Foremost in front of the retaining means 97 is arranged a sliding guide 101. The sliding guide tapers in the first direction such that the rear end 102 of the sliding guide will have the same width in a direction perpendicular to the first direction as indicated by the arrow 96 as the width of the inclined surface 98, whereas the taper brings the width to near 0. This tapered sliding guide can be seen more clearly in FIG. 21.

The second part comprises a leg 92, which is biased toward the first part 95 such that an engagement section 94 may engage the retaining means 97.

As the two parts 95,92 are mutually displaced, for example from the position illustrated in FIG. 20, the engagement section can only move to the left in relation to the first part in that the retaining means 97 will hinder any movement of the engagement section and thereby the second part 92 to the right. As the engagement section comes to the end of the sliding guide 101, the engagement section will be guided onto the first track illustrated by the plane surface 102. In the illustrated example the second track is made up of the row of retaining members 97.

As the engagement means 94 are engaged toward the tracks, i.e. the row of retaining means 97 and surface 103, the engagement means will slide on the surface 103 when the first part 95 is moved to the left in relation to the leg member 92. Due to the biasing of the leg member 92, engagement section 94 will abut the side surfaces 104 of the retaining means. If the relative movement of the two sections is stopped and the direction altered, the engagement section 94 will slide up the exposed part of the inclined surface on the retaining means and the engagement section will slide into a position equivalent to the one illustrated in FIG. 20, whereby further movement to the right becomes impossible.

If however the relative movement of the two members 95,92 is continued from the start to a position past the activation point, the entire movement can be completed without any hindrance from the retaining means 97. On the return journey the engagement means will slide over the row of retaining means 97 until it reaches the sliding guide 101, whereby access to the first track will be free again for the engagement means.

Figure 22:
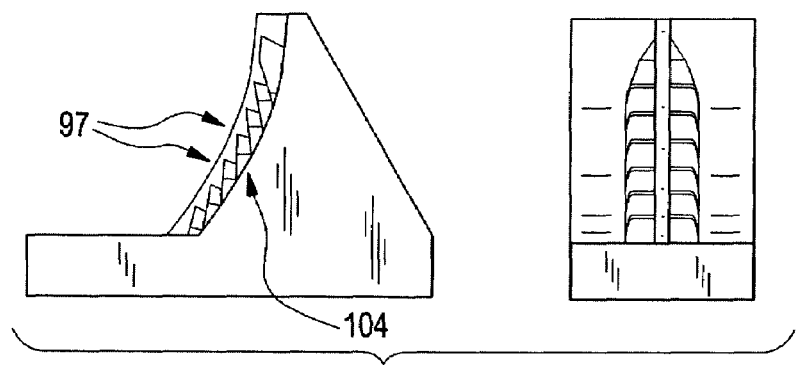
FIG. 22 illustrates the retaining means of the device.

In FIG. 22 an embodiment is illustrated where the retaining means 97 is arranged on a part of a circular member 104. When the leg 92 is arranged to pivot about a point as illustrated for example in FIG. 19, the engagement section 94 of the leg will describe part of a circle during its movement. By arranging the retaining means 97 on a circular member 104, where the distance between the pivot point and the circular member 104 is kept constant, the mechanical blocking device will function in a manner completely analogue to the one described with respect to FIG. 20.

Figure 23:
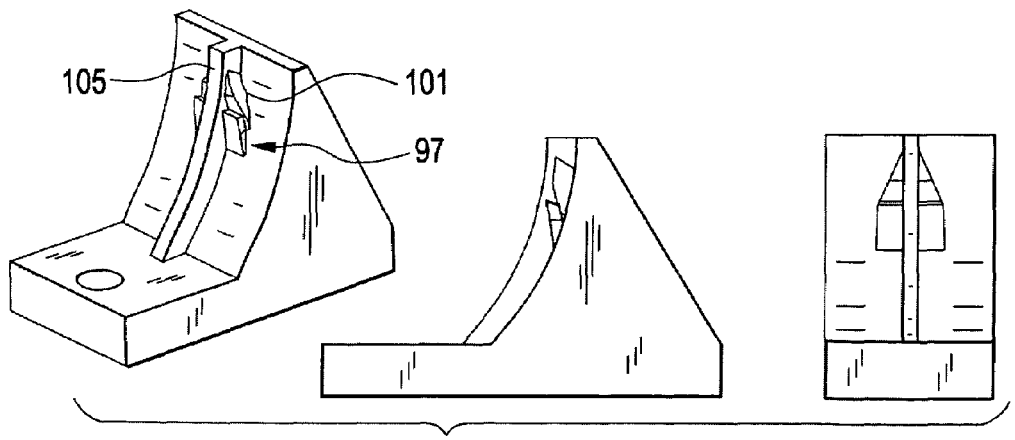
FIG. 23 illustrates a special configuration of the invention.

In FIG. 23 a special configuration of the invention is illustrated. In this configuration the mechanical blocking device is equipped with one retaining means 97 and one sliding ramp 101. This embodiment functions in exactly the same way as described above and is especially intended for cases where the construction shall insure that one event definitely takes place. The embodiment may, as is the case with all featured embodiments, be made as illustrated with two sets of tracks on either side of the middle divide 105, but may also be manufactured with only a single retaining means and a single sliding guide and a first track 103.

The invention claimed is:

1. Inhaler device (1) for dispensing a medicament comprising a housing (2), a mouthpiece (5) in the housing, a pressurized canister (6) substantially enclosed in the housing, a dose counting mechanism coupled to the pressurized canister, a mechanical actuator on the housing, wherein the mechanical actuator comprises a means (16) for engaging a bottom of the pressurized canister, a means (44, 80) for transferring actuation to the dose counting mechanism, a yoke (15, 79) disposed between and communicating with the means for engaging and the means for transferring, and a lever arm (8, 77) coupled to the yoke and disposed between the means for engaging and the means for transferring, the lever arm comprising an end operable by a user such that a movement of the lever arm transfers the movement to the yoke in a linear and/or non-linear manner thereby actuating the means for engaging and the means for transferring and dispensing measured desired dosage of the medicament from the pressurized canister through the mouthpiece to the user.

2. Inhaler device according to claim 1, wherein the movement of the pressurized canister (6) caused by said lever arm (8,77) in order to dispense a dose is shorter than the corresponding movement of said yoke (15,79).

3. Inhaler device according to claim 1, wherein the lever arm (8,77) is a pivotal section of the housing (2) constituting at least part of a top surface of the device and that the lever arm (8,77) is pivotably fastened to the housing (2) at one end of said lever arm (8,77).

4. Inhaler device according to claim 1, further comprising a member (44,54,80) optionally engaging the canister will be depressed together with depression of the lever arm (8), and that said member will transmit the depression to a dose counter for registration of a delivered dose, and that the dose counter mechanism comprises means (30,31,72,74) visible on the housing for indicating the number of dispensed doses or number of remaining doses.

5. Inhaler device according to claim 4, wherein
a groove (41) is arranged in a surface (42) of at least one of the wheels (43) at a distance from the rim, said groove (41) comprising spaced radial sections (48) connected with curved or linear sections (47) arranged such that a part of the secondary lever arm (40) is inserted and slidably arranged in said groove (41);
means (46) for urging at least one wheel to rotate.

6. Inhaler device according to claim 1, wherein a dose counter is provided, and that said dose counter comprises:

indicating means (30,31) for indicating the available content in a pressurized canister (6), which means comprises one or more indicating wheels or rollers (30,31, 72,74);
a secondary lever arm (40,54) having means (55) for engaging at least ane of the indicating wheels or rollers (30,31,72,74);
a pivotable activating member which may be integral with the lever arm (8) comprising a first linear curve or circular section (50) translating into a second linear curve or circular section (51) translating into a third linear curve or circular section (52), arranged such that the secondary lever arm (40,54) will abut and slide on said sections (50,51,52) during a count.

7. Inhaler device according to claim 1, wherein the pivotably fastened lever arm (8,77) has an engagement point (78) which engages a yoke (79), which yoke comprises a projecting member (80) which is adapted to engage a secondary lever arm having means for translating the movement of the projecting member (80) to a dose counting mechanism, where the engagement point (78) engages the yoke (79) on an upper surface (81,85,86,87) of said yoke.

8. Inhaler device according to claim 7, wherein the upper surface (81,85,86,87) of the yoke (79) is linear, such that the engagement point (78) transfers the movement of the pivotably mounted lever (77) in a linear movement to the yoke (79).

9. Inhaler device according to claim 7, wherein the upper surface of the yoke (79) is divided into two or more distinct linear or non-linear sections (85,86,87), where the lever arms engagement points' (78) travel along the second section (86) creates a substantial part of the yoke's (79) movement.

10. Inhaler device according to claim 1 comprising a mechanical return blocking arrangement where said blocking arrangement comprises two cooperating and mutually displaceable parts (92,95):

a first part (95) wherein parallel to a longitudinal axis at least one set of tracks comprising a first track (102) and a second track is provided, and that the second track comprises one or more retaining members (97) and a sliding guide (101) arranged at one end of the second track;

a second cooperating part (92) wherein a leg member comprising an engagement section (94) for engagement with the tracks provided on the first part is provided, and that said leg member is biased towards the first part (95) and that the engagement section (54) is adapted to travel in the direction of the longitudinal axis;

and further that the retaining members (97) allows the engagement section (54) of the leg member to move in a first direction towards the sliding guide (101) but blocks movement in the opposite second direction and that the engagement section (94) of the leg member slides on the sliding guide (101), whereby the engagement section (54) and thereby the leg member is directed from the second track to the first track (102).

11. Inhaler device according to claim 10, wherein in the blocking device each retaining member (97) comprises an inclined sliding surface (98) having a predetermined length along which the engagement section (94) will slide, and a step in the shape of a surface arranged at a sharp angle in relation to the sliding surface (98), said step connecting the top of one inclined sliding surface (98) and the bottom of the next sliding surface (98), such that a saw-tooth configuration is created, and such that the engagement section (54) of the leg will be retained from movement in one direction by said step.

12. Inhaler device according to claim 10, wherein the inclined sliding surface (98) overlaps an adjacent inclined sliding surface, and that the inclined sliding surface tapers perpendicular to the longitudinal axis such that the top is narrower than the bottom of the sliding surface, whereby the step at the bottom is narrower than the adjacent sliding surface at their connection point.

13. Inhaler device for dispensing a medicament from a pressurised canister (6), where said pressurized canister (6) comprises a bottom and a top, and that a valve mechanism (7) is provided in the top of said pressurized canister (6) for dispensing a medicament and that in use the pressurized canister is placed with the top downwards inside a housing proximate a mouthpiece (5), where the inhaler device comprises a mouthpiece (5) and a means for guiding and/or holding the pressurized canister, and a lever arm (8,77) comprising means (16) for engagement with the bottom end of the pressurized canister (6), such that die pressurized canister (6) is not accessible from the outside, and further that a seat for engagement with the top of the pressurized canister (6) is provided inside the housing (2), and a cap (3) is pivotally arranged on the housing and enclosing the top of the pressurized canister such that the cap (3) can be pivoted into a closed position where it covers the mouthpiece (5) and an open position where the mouthpiece (5) is accessible, and that said cap (3) further comprises means (17) for abutting the top of the pressurized canister (6) and/or for abutting the means (15,16,79) for engagement with the bottom end of the pressurized canister (6) when the cap (3) is in its closed position such that the pressurized canister (6) cannot be activated accidentally, wherein the cap no longer abuts the top of the pressurized canister or the means for engagement with the bottom end of the pressurized canister when the cap is in its open position.

14. Inhaler device for dispensing a medicament from a pressurised canister (6), where said pressurized canister (6) comprises a bottom and a top, and that a valve mechanism (7) is provided in the top of said pressurized canister (6) for dispensing a medicament and that in use the pressurized canister is placed with the top downwards inside a housing proximate a mouthpiece (5), where the inhaler device comprises a mouthpiece (5) and a means for guiding and/or holding the pressurized canister, and a lever arm (8,77) comprising means (16) for engagement with the bottom end of the pressurized canister (6), such that the pressurized canister (6) is not accessible from the outside, and further that a seat for engagement with the top of the pressurized canister (6) is provided inside the housing (2), and a cap (3) is pivotally arranged such that the cap (3) can be pivoted into a closed position where it covers the mouthpiece (5) and an open position where the mouthpiece (5) is accessible, and that said cap (3) further comprises means (17) for abutting the top of the pressurized canister (6) and/or for abutting the means (15,16,79) for engagement with the bottom end of the pressurized canister (6) when the cap (3) is in its closed position such that the pressurized canister (6) cannot be activated accidentally wherein the means (16) for engagement with the bottom of the pressurized canister comprises a yoke (15) which yoke has a canister engagement section (16) optionally having a shape corresponding to the bottom of the pressurized canister (6), and an end section, which when the cap (3) is in its closed position engages a cam (17) provided on the cap (3), such that the engagement section (16) of the yoke (15) is not in contact with the pressurized canister (6).

15. Inhaler device according to claim 13, wherein the lever arm (8,77) is guided by three tracks (9,10,11) provided on an inside of the housing (2) where the guidance comprises pins (12) arranged on the lever arm (8,77) perpendicular to the lever arm's longitudinal direction, and that said pins (12) engages the tracks (9,10,11) and preferably identical sets of tracks arranged symmetrically on either side of the lever arm; a first track or set of tracks (9) in front of the pressurized canister (6) which track is generally horizontal; a second track or set of tracks (10) provided in the yoke (15), said track also being generally horizontal and a third track or set of tracks (11) arranged behind the canister (6) and said third track (11) comprises a generally straight upper section (13) and a curved lower section (14).

16. Inhaler device according to claim 13, wherein the length of the lever arm (8) is such that when the cap (3) is closed the free end of the lever arm (8) is flush with or contained within the housing (2), and when the cap (3) is opened the free end of the lever arm (8) will project from the housing (2).

* * * * *